United States Patent [19] [11] 4,168,577
Söderkvist et al. [45] Sep. 25, 1979

[54] DEVICE FOR STEPWISE DISPLACEMENT OF A WORK-PIECE

[75] Inventors: Anton Söderkvist, Vällingby; Otto Schwarz, Johanneshov, both of Sweden

[73] Assignee: LKB-Produkter AB, Bromma, Sweden

[21] Appl. No.: 784,760

[22] Filed: Apr. 5, 1977

Related U.S. Application Data

[63] Continuation of Ser. No. 630,759, Nov. 11, 1975, abandoned.

[30] Foreign Application Priority Data

Nov. 26, 1974 [SE] Sweden ............................... 7414819

[51] Int. Cl.² ............................................. G01B 5/00
[52] U.S. Cl. ..................................... 33/180 R; 310/17

[58] Field of Search ...................... 310/17, 23, 20, 26, 310/15, 30; 33/180, DIG. 19

[56] References Cited

U.S. PATENT DOCUMENTS 3,217,218  11/1965  Steele ..................................... 310/26

Primary Examiner—Richard E. Aegerter
Assistant Examiner—Willis Little
Attorney, Agent, or Firm—Fisher, Christen & Sabol

[57] ABSTRACT

The present invention refers to a device for stepwise displacement of a work-piece or a similar body, the device comprising a rod made from a reversibly expanding or compressing material coupled to an activation device whereby the rod has its ends resting in clamping brackets to be clamped alternatively at the expansion or compressing of the rod.

5 Claims, 3 Drawing Figures

DEVICE FOR STEPWISE DISPLACEMENT OF A WORK-PIECE

This is a continuation of application Ser. No. 630,759, filed Nov. 11, 1975 now abandoned.

With a number of areas of application it is desirable to provide small well defined displacements of a work-piece. This could for instance be desirable when the work-piece is subject to treatment by means of a tool. Another area of use is the movement of a knife or a sample in a microtome or an ultramicrotome where the knife before cutting off the sample is to be located closed to the sample or vice versa. A method known per se for solving this problem is described e.g. in the U.S. Pat. No. 2,506,141 which describes a device comprising a magnetostrictive rod which is surrounded by a coil and rests in two brackets in which the rod electrically can be clamped. If the rod hereby is made to expand while being clamped in its one end and thereafter is made to compress itself while being clamped at its other end each such cycle will imply a stepwise movement of the rod. Such a device would be very suitable for a controlled feeding of the knife in a microtome since it in principle gives small and very exact steps of movement. The drawback is, however, that in the designs known per se it is not possible to make the steps as small as desirable. Thus the above mentioned patent gives the figure $10^{-6}$ m as the length of each step whereas the use in an ultramicrotome would require steplengths which would be in the order of $10^{-7}$ m. The reason for not obtaining such small steps hitherto is that these small steps put very high requirements on the clamping brackets at the ends of the rod. Thus it is required that the friction when the rod is moving in the bracket must not be too high and furthermore the clamping must be very effective and the clamping operation must not involve any movement of the rod. It is an object of the present invention to provide a device in accordance with the above designed principle whereby the brackets are designed so as to admit the very small feeding steps required in an ultramicrotome. The characteristics of the invention will appear from the claims attached to the specification.

The device will now be described in detail, reference being made to the enclosed drawing in which.

Figure 1:
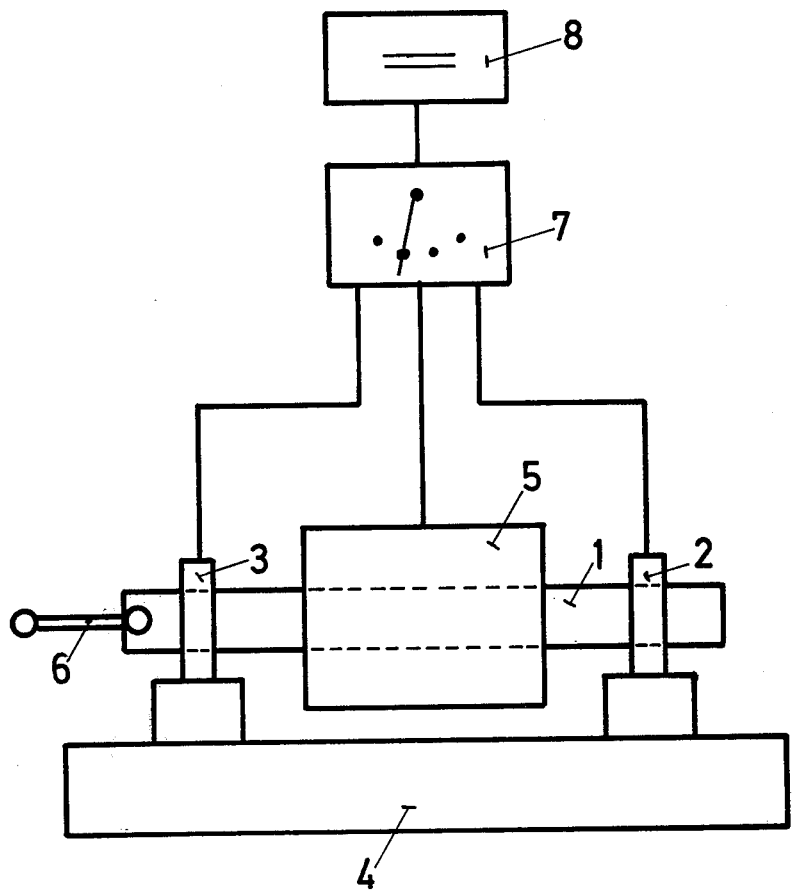
FIG. 1 shows a diagram of a device according to the invention

In FIG. 1, reference 1 denotes a rod which at least in its central part is made from a magnetostrictive material. The rod is resting at its ends in two electrically operated clamping brackets 2 and 3 respectively which are arranged on a base 4. The central part of the rod is surrounded by a coil 5 and furthermore one end of the rod is provided with an arm 6 which is to be attached to the mechanical element to be driven by the rod. The electrically clamping brackets 2 and 3 and the coil 5 surrounding the rod are activated from a power supply 8 via a switch 7. When the rod is to be moved leftwards in the figure the activation of the clamping brackets and the coil is made according to the following sequence:

1. Bracket 2 clamped, bracket 3 released, coil 5 unactivated.
2. Bracket 2 clamped, bracket 3 released, coil 5 activated.
3. Bracket 2 clamped, bracket 3 clamped, coil 5 activated.
4. Bracket 2 released, bracket 3 clamped, coil 5 activated.
5. Bracket 2 released, bracket 3 clamped, coil 5 unactivated.

Then this sequence is repeated by activating the clamping of bracket 2, whereby each sequence will imply a stepwise displacement of the rod leftwards. In a similar way the rod could of course be displaced rightwards. The device so far described is known per se.

Figure 2:
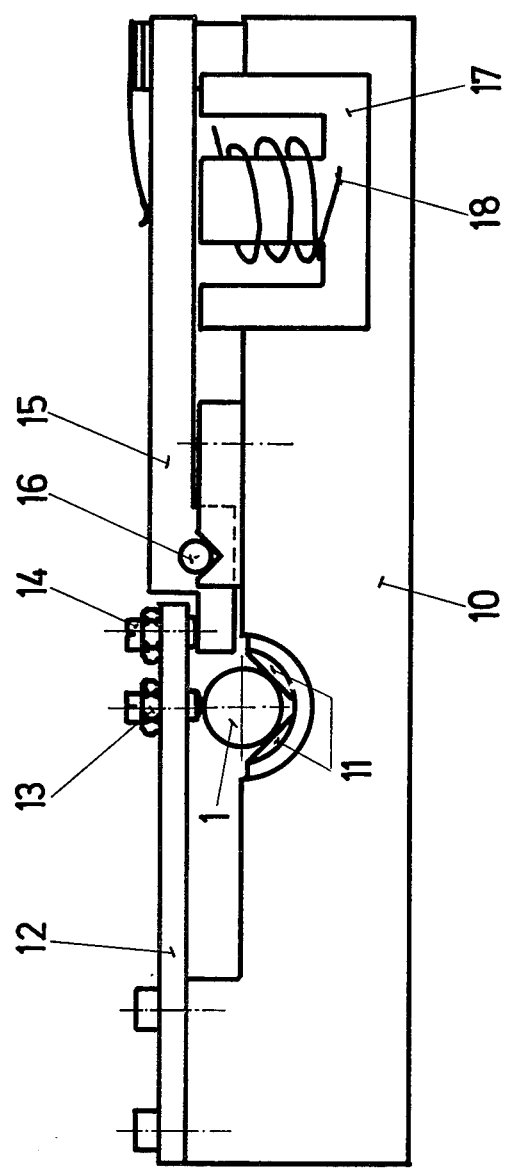
FIG. 2 is a section through one of the clamping devices for the rod included in the device and FIG. 3 is a perspective view of the clamping device.
Figure 3:
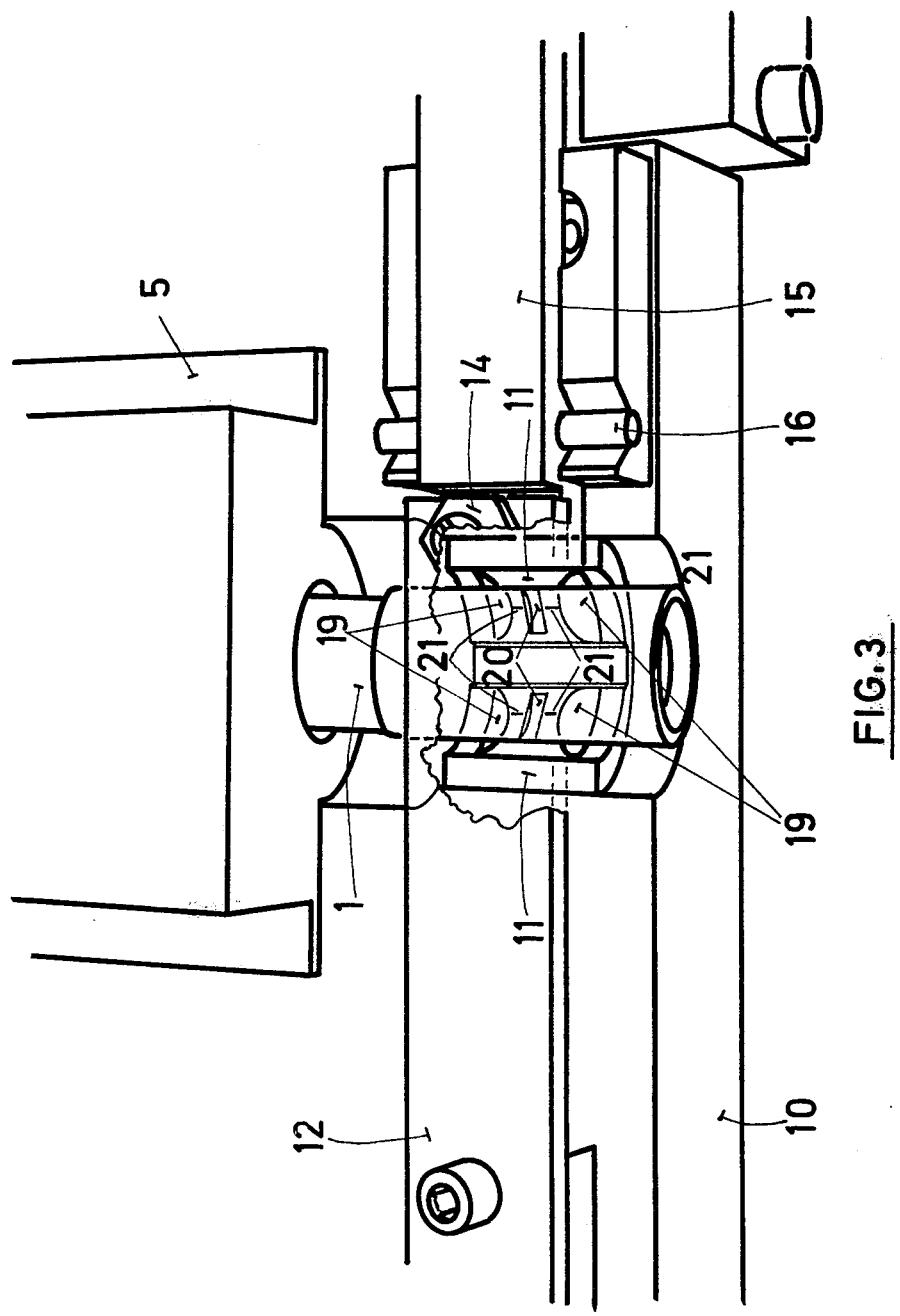

In FIG. 2, which shows a section through the rod 1 at one of the brackets 2 or 3, reference 10 denotes a base on which the rod 1 is resting in a V-shaped groove 11. The rod is clamped in the groove by means of a screw 13 arranged on a spring 12. The spring is provided with a second screw 14 resting on an arm 15 journalled on an axis 16. Upon activation of a coil 18 arranged on a magnet core 17 the arm 15 will turn around the axis 16 and lift spring 12 so that the rod is released from its brackets. The details of the bracket appear from FIG. 3 where corresponding parts have the same reference as in FIG. 2. It appears from FIG. 3 that the V-shaped groove 11, in which the rod is resting along the surfaces 21, is provided with cavities 19 at its ends as well as with central cavities 20. These cavities 20 are arranged in the same vertical plane as the touching point of the screw 13. The advantage of these grooves 20 is that the contact surfaces 21 are shortened whereby the friction between the rod and the groove is decreased and furthermore the grooves prevent the rod from tilting or moving when the screw 13 is brought into contact with the rod. A further advantage of the invention is that by making the screw 14 move along the arm 15 one makes sure that the spring 12 is moved straight upwards whereby it is avoided that the rod is moved at this operation.

We claim:

1. Device for incremental movement of a work-piece or similar article by stepwise displacement comprising;
   i. an elongated rod formed from a reversibly compressible or expandable material;
   ii. a pair of horizontally spaced clamped systems for supporting said rod, each of said clamping systems including:
      a. a block mounted on a base, said block being provided with two pairs of flat surfaces lying respectively on opposite sides of a vertical plane and at an angle with respect to said plane, the two flat surfaces of each pair lying axially spaced from each other in a common plane to define a cavity in said block between the two surfaces, the flat surfaces of one pair being generally disposed opposite to the flat surfaces of the other pair to provide supporting contact with said rod at four locations spaced from each other, two of said locations lying spaced axially from a plane transverse to the axis of the rod, the other two locations lying axially spaced from the other side of said transverse plane;
      b. an elongated spring arm having one end for clamping contact with said rod at a location lying in said transverse plane and generally on the side of the rod opposite to said four locations, the other end of said elongated spring arm being fixedly secured to said base, and;
      c. electrical solenoid actuator means, said electrical solenoid actuator means comprising a lever arm of the first class pivotally supported on said base, one end of the lever arm being arranged in engagement with said one end of the spring arm, the other end of the lever arm being in engagement with an electrically energized solenoid for withdrawing said one end of the spring arm from said clamping contact with the rod, for said stepwise displacement.

2. Device according to claim 1, characterized in, that the rod is made from magnetostrictive material and the activating means consists of an electrically energizable coil connected with the rod so that a magnetic field can be applied across the rod.

3. Device according to claim 1, characterized in, that the rod is made from piezo-electric material and the activating means consists of means for supplying an electrical current across the rod.

4. Device according to claim 1, characterized in, that the rod is made from a material expanding when heated, the activating means consisting of an electrically energizable heater coil.

5. Device according to claim 1, characterized in, that the rod is made from an elastic material the activating device being a device for applying forces along the longitudinal axis of the rod.

* * * * *